United States Patent
Lin et al.

(10) Patent No.: US 12,324,087 B2
(45) Date of Patent: Jun. 3, 2025

(54) BEAM EQUIPMENT CONTROLLING SYSTEM AND BEAM EQUIPMENT CONTROLLING METHOD

(71) Applicant: Heron Neutron Medical Corp., Zhubei (TW)

(72) Inventors: Chih-Chung Lin, Zhubei (TW); Siao-Cing Liou, Zhubei (TW); Shan-Haw Chiou, Zhubei (TW)

(73) Assignee: HERON NEUTRON MEDICAL CORP., Zhubei (TW)

( * ) Notice: Subject to any disclaimer, the term of this patent is extended or adjusted under 35 U.S.C. 154(b) by 205 days.

(21) Appl. No.: 18/334,808

(22) Filed: Jun. 14, 2023

(65) Prior Publication Data
US 2024/0268015 A1    Aug. 8, 2024

(30) Foreign Application Priority Data
Feb. 4, 2023    (TW) ................. 112103962

(51) Int. Cl.
*H05H 7/06*    (2006.01)
*A61N 5/10*    (2006.01)
*H05H 13/00*    (2006.01)

(52) U.S. Cl.
CPC ............. *H05H 7/06* (2013.01); *A61N 5/1048* (2013.01); *A61N 5/1078* (2013.01);
(Continued)

(58) Field of Classification Search
CPC ........ H05H 1/18; H05H 13/00; H05H 13/005; H05H 13/02; H05H 13/04; H05H 7/06;
(Continued)

(56) References Cited

U.S. PATENT DOCUMENTS

2018/0169440 A1    6/2018  Liu et al.
2022/0070994 A1*   3/2022  Snitchler ............. A61N 5/1075

FOREIGN PATENT DOCUMENTS

JP    2018-528034 A       9/2018
WO    WO 2022/017193 A1   1/2022

OTHER PUBLICATIONS

European Search Report for European Application No. 23183835.0, dated Dec. 14, 2023.

* cited by examiner

*Primary Examiner* — Henry Luong
(74) *Attorney, Agent, or Firm* — Birch, Stewart, Kolasch & Birch, LLP

(57) ABSTRACT

A beam equipment controlling method is provided. The method includes: proton beam regulatory steps, including: generating a first proton beam after confirming that the generating conditions are met, and marking the proton beam regulatory steps as completed after confirming that the first proton beam meets the specifications; neutron beam regulatory steps, including: generating a first neutron beam after confirming that the proton beam regulatory steps are completed and the generating conditions are met, confirming that the first neutron beam meets specifications, and marking the neutron beam regulatory steps as completed after turning off the cyclotron system; and treatment regulatory steps, including: generating a second neutron beam after confirming that the neutron beam regulatory steps are completed and the treatment-beam generating conditions are met, confirming that the second neutron beam meets treatment needs; and marking the treatment regulatory steps as completed after turning off the cyclotron system.

14 Claims, 5 Drawing Sheets

(52) U.S. Cl.
CPC ... *H05H 13/005* (2013.01); *A61N 2005/1087* (2013.01); *A61N 2005/109* (2013.01)

(58) Field of Classification Search
CPC ................ A61N 5/1048; A61N 5/1078; A61N 2005/1087; A61N 2005/109
See application file for complete search history.

BEAM EQUIPMENT CONTROLLING SYSTEM AND BEAM EQUIPMENT CONTROLLING METHOD

CROSS REFERENCE TO RELATED APPLICATIONS

This Application claims priority of Taiwan patent application No. 112103962, filed on Feb. 4, 2023, the entirety of which is incorporated by reference herein.

BACKGROUND OF THE INVENTION

Field of the Invention

The present invention relates to a beam equipment controlling system and a beam equipment controlling method.

Description of the Related Art

A piece of beam equipment is equipment that generates a beam that has energy. They are often used in the field of medicine, such as in Boron Neutron Capture Therapy (BNCT). Since the beam has penetrability and thus has certain risks, the use of beam equipment needs to be regulated to ensure that it is used under safe conditions.

When treatment is performed using a beam, it is necessary to successively undergo Quality Assurance (QA) and Quality Control (QC) of proton beams and neutron beams to ensure that the treatment neutron beam is stable and safe. After all of the test proton beams and the test neutron beams have completed QA/QC, the treatment neutron beams can be generated to perform irradiation treatment. However, in the current conventional technology, there is no system that is capable of performing the QA/QC procedure control for proton beams and neutron beams. Therefore, in practice, there are situations where harm may be caused by errors in the procedure that can lead to safety risks, wasted time and energy, or mechanical failure.

In view of the issues described above, the present disclosure provides a beam equipment controlling system and method, which can control the generation of proton beams and neutron beams together to ensure that the procedures in each course of treatment are correct, to improve the safety, and to reduce the risk of personal injury and equipment damage. In addition, by using the beam equipment controlling system and method disclosed in the present disclosure, unnecessary time consumption and energy consumption can be reduced and the accuracy can be improved.

BRIEF SUMMARY OF THE INVENTION

An embodiment of the present invention provides a beam equipment controlling system for controlling a cyclotron system. The beam equipment controlling system comprises a storage device configured to store a treatment controlling application program and at least one processor configured to execute the treatment controlling application program to implement following modules: a proton beam regulatory module, a neutron beam regulatory module, and a treatment regulatory module. When it is implemented, the proton beam regulatory module performs the following steps: determining whether to allow the cyclotron system to generate a first proton beam; and after confirming that the first proton beam meets first proton beam specifications, making the cyclotron system stop outputting the first proton beam and marking that a proton beam regulatory step has been completed. When it is implemented, the neutron beam regulatory module performs the following steps: after confirming that the proton beam regulatory step is marked as completed and that a state of the cyclotron system meets neutron-beam generating conditions, allowing the cyclotron system to generate a first neutron beam; confirming that the first neutron beam meets first neutron beam specifications; and after making the cyclotron system stop outputting the first neutron beam, marking that a neutron beam regulatory step has been completed. When it is implemented, the treatment regulatory module performs the following steps: after confirming that the neutron beam regulatory step is marked as completed and that a state of the cyclotron system meets treatment-beam generating conditions, ordering the cyclotron system to generate a second neutron beam; confirming whether the second neutron beam meets treatment needs; and after making the cyclotron system stop outputting the second neutron beam, marking that a treatment regulatory step has been completed.

An embodiment of the present invention provides a beam equipment controlling method for controlling a cyclotron system. The beam equipment controlling method comprises proton beam regulatory steps, neutron beam regulatory steps, and treatment regulatory steps. The proton beam regulatory steps comprise: determining whether to allow the cyclotron system to generate a first proton beam; and after confirming that the first proton beam meets first proton beam specifications, making the cyclotron system stop outputting the first proton beam and marking that the proton beam regulatory steps have been completed. The neutron beam regulatory steps comprise: after confirming that the proton beam regulatory steps are marked as completed and that a state of the cyclotron system meets neutron-beam generating conditions, allowing the cyclotron system to generate a first neutron beam; confirming that the first neutron beam meets first neutron beam specifications; and after making the cyclotron system stop outputting the first neutron beam, marking that the neutron beam regulatory steps have been completed. The treatment regulatory steps comprise: after confirming that the neutron beam regulatory steps are marked as completed and that a state of the cyclotron system meets treatment-beam generating conditions, ordering the cyclotron system to generate a second neutron beam; confirming whether the second neutron beam meets treatment needs; and after making the cyclotron system stop outputting the second neutron beam, marking that the treatment regulatory steps have been completed.

DETAILED DESCRIPTION OF THE INVENTION

Hereinafter, embodiments according to the present invention will be described in detail with reference to the accompanying drawings. The disclosed embodiments are illustrative only, and the scope of the present invention is not limited thereto.

Figure 1:
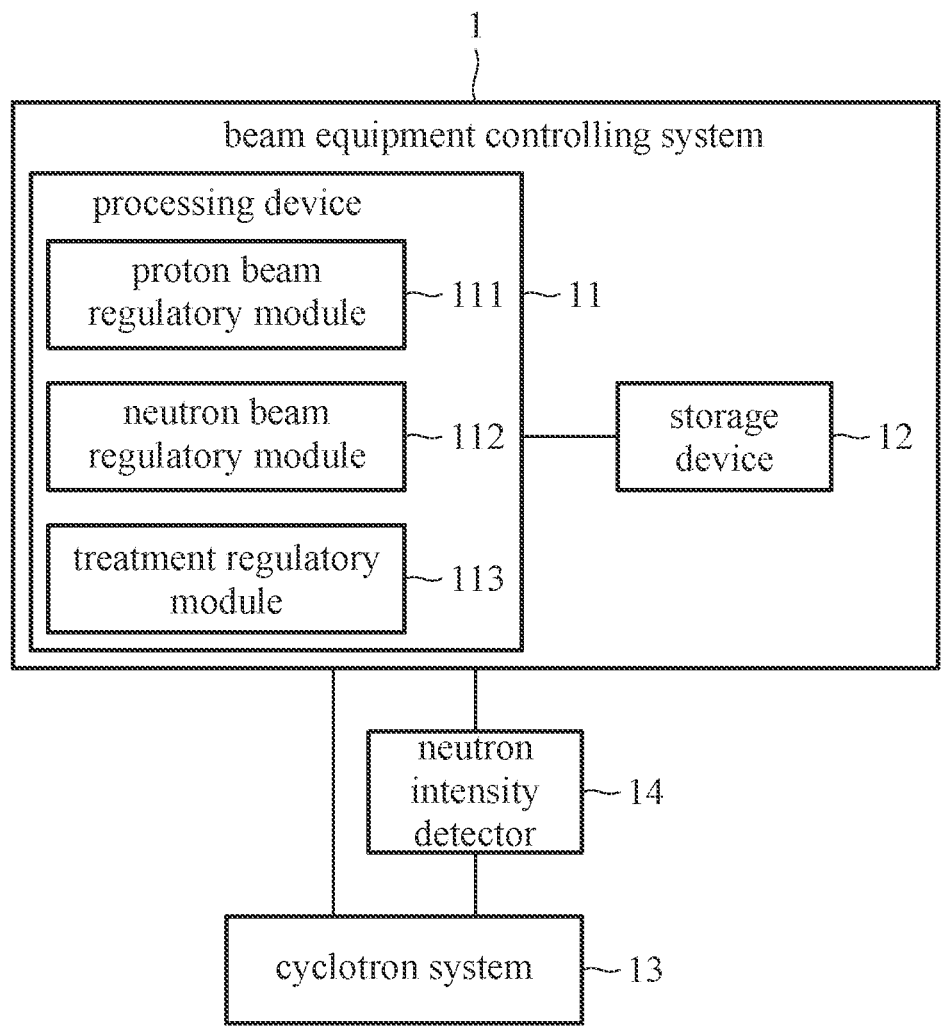
FIG. 1 illustrates a block diagram of a beam equipment controlling system 1 of an embodiment 1 of the present invention.

An embodiment 1 of the present invention will be described with reference to FIG. 1. The embodiment 1 of the present invention is a beam equipment controlling system 1. The beam equipment controlling system 1 can execute a beam equipment controlling program stored in a storage device 12 by a processing device 11 to implement a proton beam regulatory module 111, a neutron beam regulatory module 112, and a treatment regulatory module 113 to control a cyclotron system 13.

The processing device 11 is, for example, a logic operation device of hardware such as central processing unit (CPU), digital signal processor (DSP), application specific integrated circuit (ASIC), or field programmable gate array (FPGA). Alternatively, the processing device 11 may also be implemented by an electronic circuit, such as implemented by a microcontroller unit (MCU), a single chip, a single circuit, a composite circuit, a programmable processor, a parallel programmable processor, a logic IC, or a gate array (GA).

The storage device 12 is a device for storing data. The specific examples of the storage device 12 include solid state drive (SSD), hard disk drive (HDD), flash memory and the like. The beam equipment controlling application program is stored in the storage device 12, and is loaded by the processing device 11 to implement the proton beam regulatory module 111, the neutron beam regulatory module 112, and the treatment regulatory module 113.

In addition, the beam equipment controlling application program can also first be loaded from the storage device 12 into a memory (not shown) for temporarily storing data, and then executed by the processing device 11. The specific example of the memory includes static random access memory (SRAM) or dynamic random access memory (DRAM).

In order to generate a treatment neutron beam that is safe and effective, it is necessary to ensure that a test proton beam and a test neutron beam have been generated correctly. The beam equipment controlling system 1 first confirms that the test proton beam (first proton beam P1) generated by the cyclotron system 13 meets the specifications through the proton beam regulatory module 111. Then, the beam equipment controlling system 1 confirms that the test neutron beam (first neutron beam) generated by the cyclotron system 13 meets the specifications through the neutron beam regulatory module 112. The cyclotron system 13 is allowed to generate a treatment neutron beam (the second neutron beam) through the treatment regulatory module 113 only after the confirming on the test proton beam and test neutron beam are completed successively. The steps performed in the proton beam regulatory module 111, the neutron beam regulatory module 112, and the treatment regulatory module 113 are described in detail below.

First, the steps performed by the proton beam regulatory module 111 will be described. When the cyclotron system 13 sends a request to the beam equipment controlling system 1 to generate the first proton beam, the beam equipment controlling system 1 activates the proton beam regulatory module 111. The proton beam regulatory module 111 may determine whether the request to generate the first proton beam can be allowed according to safety conditions. For example, a safety condition may be that the user performs an input using an input device (not shown) connected to the processing device 11 after confirming that the environment is safe, such as inputting specific parameters by a keyboard, or clicking a specific button on a display by a mouse. Alternatively, in the case where the cyclotron system 13 has a plurality of irradiation rooms, the safety condition may be that the cyclotron system 13 is not occupied by other irradiation rooms. For example, when the cyclotron system 13 is occupied by other courses of treatment, the proton beam regulatory module 111 will reject the request of the cyclotron system 13 to generate the first proton beam. At this time, the cyclotron system 13 waits for the proton beam regulatory module 111 to allow generating the first proton beam.

After the proton beam regulatory module 111 allows the cyclotron system 13 to generate the first proton beam, the cyclotron system 13 confirms that the current state meets proton-beam generating conditions, wherein the proton-beam generating conditions are conditions that the cyclotron system 13 is suitable for generating the proton beam. That is, the cyclotron system 13 is adjusted to a state that the proton beam can be generated. The cyclotron system 13 and the proton-beam generating conditions of the present embodiment will be described below.

Figure 2:
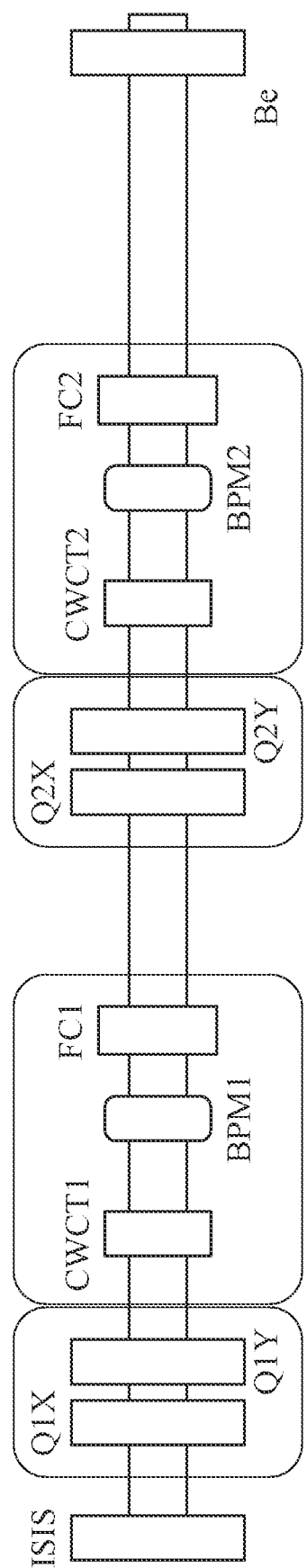
FIG. 2 illustrates a structural schematic diagram of a cyclotron system 13.

The structural schematic diagram of the cyclotron system 13 of the present embodiment is as shown in FIG. 2. Quadrupole magnets Q1X, Q1Y, Q2X, and Q2Y are configured to focus the ion beam generated by an ion source ISIS. Continuous wave current transformers CWCT1 and CWCT2 are configured to monitor current curves. Beam profile monitors BPM1 and BPM2 are configured to monitor the profile of the beam. The switching state of a first Faraday cup FC1 determines whether the cyclotron system 13 can generate the proton beam. The switching states of the first Faraday cup FC1 and a second Faraday cup FC2 determine whether the beam generated by the ion source ISIS of the cyclotron system 13 can pass through and hit the beryllium target to generate the neutron beam.

In the present embodiment, the proton-beam generating conditions include that the first Faraday cup FC1 is turned on and the second Faraday cup FC2 is turned off. The proton-beam generating conditions are not limited thereto. Any conditions may be the proton-beam generating condition as long as they are conditions enabling the cyclotron system 13 to generate the proton beam.

When the cyclotron system 13 cannot meet the proton-beam generating conditions within a period of time, the beam equipment controlling system 1 can be notified to maintain and tune the cyclotron system 13 (e.g., the beam equipment controlling system 1 sends a warning to inform the user that the system is abnormal). When the cyclotron system 13 confirms that the proton-beam generating conditions are met, the cyclotron system 13 controls the ion source ISIS to inject current to generate a current proton beam as the first proton beam P1 for testing.

Next, the cyclotron system 13 confirms whether the first proton beam P1 meets first proton beam specifications. In the present embodiment, the first proton beam specifications include that the values of the continuous wave current transformers CWCT1 and CWCT2 reach the set values, and the beam profile monitors BPM1 and BPM2 meet the specifications. When the cyclotron system 13 confirms that the first proton beam P1 does not meet the first proton beam specifications within a period of time, it may notify the beam equipment controlling system 1 to maintain and tune the cyclotron system 13. When the cyclotron system 13 confirms that the first proton beam P1 meets the first proton beam specifications, it reports the result indicating that the QA/QC of the first proton beam P1 has been completed to the beam equipment controlling system 1.

After the proton beam regulatory module 111 receives the result of "the QA/QC of the first proton beam P1 has been completed," the proton beam regulatory module 111 makes the cyclotron system 13 stop outputting the first proton beam. Next, the proton beam regulatory module 111 marks that the proton beam regulatory steps have been completed. The way for marking that the steps have been completed may include, for example, creating a memory space for marking that whether the proton beam regulatory steps, the neutron beam regulatory steps, and the treatment regulatory steps have been completed in a memory readable for the processing device 11, and marking with values 0 and 1. The steps that have been completed are marked as 1, the steps that not have been completed are marked as 0, and the default value is 0. Alternatively, the marking described above can also be stored in the storage device 12. After the proton beam regulatory module 111 marks that the proton beam regulatory steps have been completed, it cancels the allowance of the cyclotron system 13 to generate the first proton beam P1.

Next, the steps performed by the neutron beam regulatory module 112 will be described. After the proton beam regulatory module 111 marks that the proton beam regulatory steps have been completed, the beam equipment controlling system 1 activates the neutron beam regulatory module 112. The neutron beam regulatory module 112 needs to first confirm that the proton beam regulatory steps are marked as completed. Then, the neutron beam regulatory module 112 requests the cyclotron system 13 to generate the first neutron beam. The cyclotron system 13 confirms that the current state meets the neutron-beam generating conditions. The neutron-beam generating conditions are conditions that the cyclotron system 13 is suitable for generating the neutron beam. In the present embodiment, the neutron-beam generating conditions include that the first Faraday cup FC1 is turned on, and the second Faraday cup FC2 is turned on. The neutron-beam generating conditions are not limited thereto. Any conditions may be the neutron-beam generating condition as long as they are conditions enabling the cyclotron system 13 to generate the neutron beam.

When the cyclotron system 13 determines that the neutron-beam generating conditions cannot be met within a period of time, it will notify the beam equipment controlling system 1 to maintain and tune the cyclotron system 13. When the cyclotron system 13 confirms that the neutron-beam generating conditions are met, the cyclotron system 13 controls the ion source ISIS to inject the current generate the first neutron beam as the test neutron beam.

Next, the neutron beam regulatory module 112 confirms whether the first neutron beam meets first neutron beam specifications. In the present embodiment, the first neutron beam specifications include a specification of neutron intensity. The neutron beam regulatory module 112 may confirm whether the first neutron beam meets the neutron intensity via a neutron intensity detector 14. In the present embodiment, the neutron intensity detector 14 is configured to be capable of detecting the neutron beam generated by the cyclotron system 13, and transmitting the detecting result to the beam equipment controlling system 1 after detecting the neutron intensity of the neutron beam, so that the neutron beam regulatory module 112 and the treatment regulatory module 113 can read the detecting result.

When the first neutron beam does not meet the first neutron beam specifications within a period of time, the beam equipment controlling system 1 notifies the cyclotron system 13 of this abnormal state, so as to maintain and tune the cyclotron system 13. When the first neutron beam meets the first neutron beam specifications, the beam equipment controlling system 1 notifies the cyclotron system 13 of this result, and makes the cyclotron system 13 stop outputting the first neutron beam to end the test of the neutron beam. When make the cyclotron system 13 stop outputting the first neutron beam, for example, the beam equipment controlling system 1 notifies the cyclotron system 13 to cancel the allowance to generate the first neutron beam, and to turn off the ion source ISIS, the first Faraday cup FC1, and the second Faraday Cup FC2. After the ion source ISIS, the first Faraday cup FC1, and the second Faraday cup FC2 are turned off, the cyclotron system 13 notifies the beam equipment controlling system 1 that the cyclotron system 13 has been turned off. The neutron beam regulatory module 112 marks that the neutron beam regulatory steps have been complete.

Next, the steps performed by the treatment regulatory module 113 will be described. After the neutron beam regulatory module 112 marks that the neutron beam regulatory steps have been completed, the beam equipment controlling system 1 activates the treatment regulatory module 113. The treatment regulatory module 113 first confirms that the proton beam regulatory steps and the neutron beam regulatory steps are marked as completed, and the current state of the cyclotron system 13 meets treatment-beam generating conditions. The treatment-beam generating conditions are states that the cyclotron system 13 is on standby and can start neutron beam irradiation treatment at any time. In the present embodiment, the treatment-beam generating conditions are that the first Faraday cup FC1 is turned on, the second Faraday cup FC2 is turned on, and the cyclotron system 13 is in a standby state (i.e., the state that can control the ion source ISIS to inject the current any time to generate the treatment neutron beam).

Next, the beam equipment controlling system 1 waits for a treatment activating command. The treatment activating command is entered by a user (e.g., medical personnel). For example, the user inputs a specific parameter or presses a specific button to input the treatment activating command to the beam equipment controlling system 1. In addition, while waiting for the treatment activating command, the treatment regulatory module 113 may also require the user to input treatment needs. The treatment needs are specifications of the treatment neutron beam (the second neutron beam), and are determined according to the treatment plan instructed by the doctor. In the present embodiment, the treatment regulatory module 113 requires the user to input the tumor prescription dose and treatment plan instructed by the doctor as the treatment needs. The treatment regulatory module will calculate the required treatment time according to the treatment needs input by the user. However, since the irradiation time may be adjusted at any time according to the irradiation situation in practice, the treatment needs in the present embodiment and the method of determining whether the treatment needs are met described later are just examples. The treatment needs and the way to achieve the treatment needs can be designed differently according to the practical needs. For example, the prescribed dose of normal tissue prescribed by the doctor can also be used as the treatment needs, and the parameters are inspected and the irradiation time is adjusted during the operation of the cyclotron system 13 described later.

When the beam equipment controlling system 1 receives the treatment activating command issued by the user, after the beam equipment controlling system 1 transmits the treatment needs to the cyclotron system 13, and orders the cyclotron system 13 to control the ion source ISIS to inject the current to generate the treatment neutron beam (second neutron beam).

The cyclotron system 13 operates and begins to generate the second neutron beam. If the cyclotron system 13 cannot operate normally within a period of time, it is needed to notify the beam equipment controlling system 1. The user (e.g., medical personnel) decides whether to stop the treatment (i.e., make the treatment regulatory module 113 stop performing treatment) according to the received information. After the cyclotron system 13 operates normally, the treatment regulatory module 113 continuously confirms whether the generated second neutron beam meets the treatment needs. In some embodiments, the continuous wave current transformers CWCT1 and CWCT2 may be used to measure the proton number generated by the cyclotron system 13 respectively to obtain a first current value or a second current value corresponding to the proton number. Afterwards, the first current value or the second current value is compared with a preset first current value or a preset second current value, wherein the preset first current value or the preset second current value functions as a criterion of whether the treatment needs are met. Alternatively, the neutron intensity detector may be used to measure a neutron number generated by the cyclotron system 13 to obtain the neutron counting rate. The neutron counting rate is compared with the preset neutron number condition, wherein the preset neutron number condition functions as a criterion of whether the treatment needs are met. As used herein, the term "neutron counting rate" refers to the neutron number measured by a device such as a proportional counter. In some embodiments, the neutron number can be derived from the pulsation number measured in the proportional counter. In addition, as used herein, the neutron number condition is a condition or a value under which the neutron number can be derived. For example, the neutron counting rate is related to the proton current. When the current is greater, more neutrons are generated. Therefore, observing the current can also learn the quantity of the neutron number. As used herein, the neutron number condition may be the neutron counting rate, a neutron yield factor described below, a neutron flux, or any value related to the neutron number. In the present embodiment, before the irradiation time ends, the treatment regulatory module 113 divides the neutron counting rate by the first current value to obtain a first neutron yield factor, and compares the first neutron yield factor with a first preset neutron yield factor. When the difference between the first neutron yield factor and the first preset neutron yield factor is greater than or equal to a first neutron yield factor threshold value, the treatment regulatory module 113 will send a notification. It is up to the user (e.g., medical personnel) to decide whether to stop the treatment (i.e., make the treatment regulatory module 113 stop performing the treatment). In some embodiments, the first neutron yield factor threshold value may be 5% of the first preset neutron yield factor, but the present disclosure is not limited thereto. Alternatively, the neutron counting rate may be first converted into the neutron flux, and the neutron flux may be divided by the first current value to obtain the first neutron yield. As used herein, the term "neutron flux" refers to the neutron number passing through a unit area per unit time. In some embodiments, "neutron flux" is equal to the product of neutron density and its average velocity. Next, the first neutron yield can be compared with the first preset neutron yield. When the difference between the first neutron yield and the first preset neutron yield is greater than or equal to a first neutron yield threshold value, the treatment regulatory module 113 will send a notification. It is up to the user (e.g., medical personnel) to decide whether to stop the treatment (i.e., make the treatment regulatory module 113 stop performing the treatment). Moreover, confirm whether the neutron count rate meets the treatment needs through the neutron intensity detector, so as to confirm whether the second neutron beam meets the treatment needs.

After the irradiation time is over, the treatment regulatory module 113 orders the cyclotron system 13 to stop outputting the second neutron beam, and detects whether the cyclotron system 13 has stopped outputting the second neutron beam. After the cyclotron system 13 stops outputting the second neutron beam, the treatment regulatory module 113 marks that the treatment regulatory steps have been completed.

An embodiment 2 of the present invention will be described below. The embodiment 2 of the present invention is a beam equipment controlling method for controlling a cyclotron system. The beam equipment controlling method includes proton beam regulatory steps, neutron beam regulatory steps, and treatment regulatory steps. The steps described above may be implemented through a beam equipment controlling system connected with the cyclotron system. The beam equipment controlling system includes a processing device, the processing device is configured to perform a software stored in a storage device.

The processing device is, for example, a logic operation device of hardware such as central processing unit (CPU), digital signal processor (DSP), application specific integrated circuit (ASIC), or field programmable gate array (FPGA). Alternatively, the processing device may also be implemented by an electronic circuit, such as implemented by a microcontroller unit (MCU), a single chip, a single circuit, a composite circuit, a programmable processor, a parallel programmable processor, a logic IC, or a gate array (GA). The storage device is, for example, a solid state drive (SSD), a hard disk drive (HDD), a flash memory, a static random access memory (SRAM), or a dynamic random access memory (DRAM) and the like.

Figure 4:
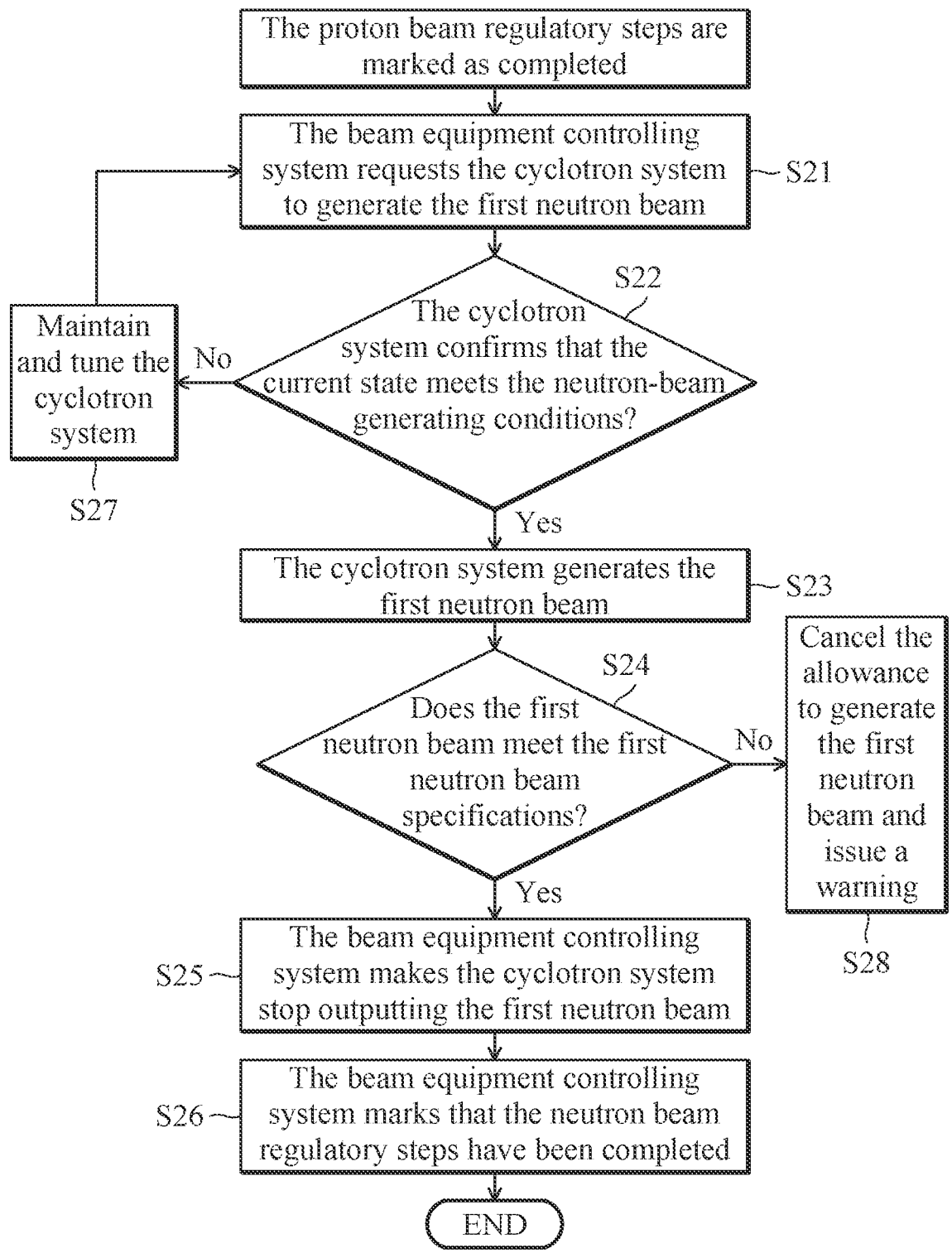
FIG. 4 illustrates a flow chart of neutron beam regulatory steps of the beam equipment controlling method of the embodiment 2 of the present invention.
Figure 5:
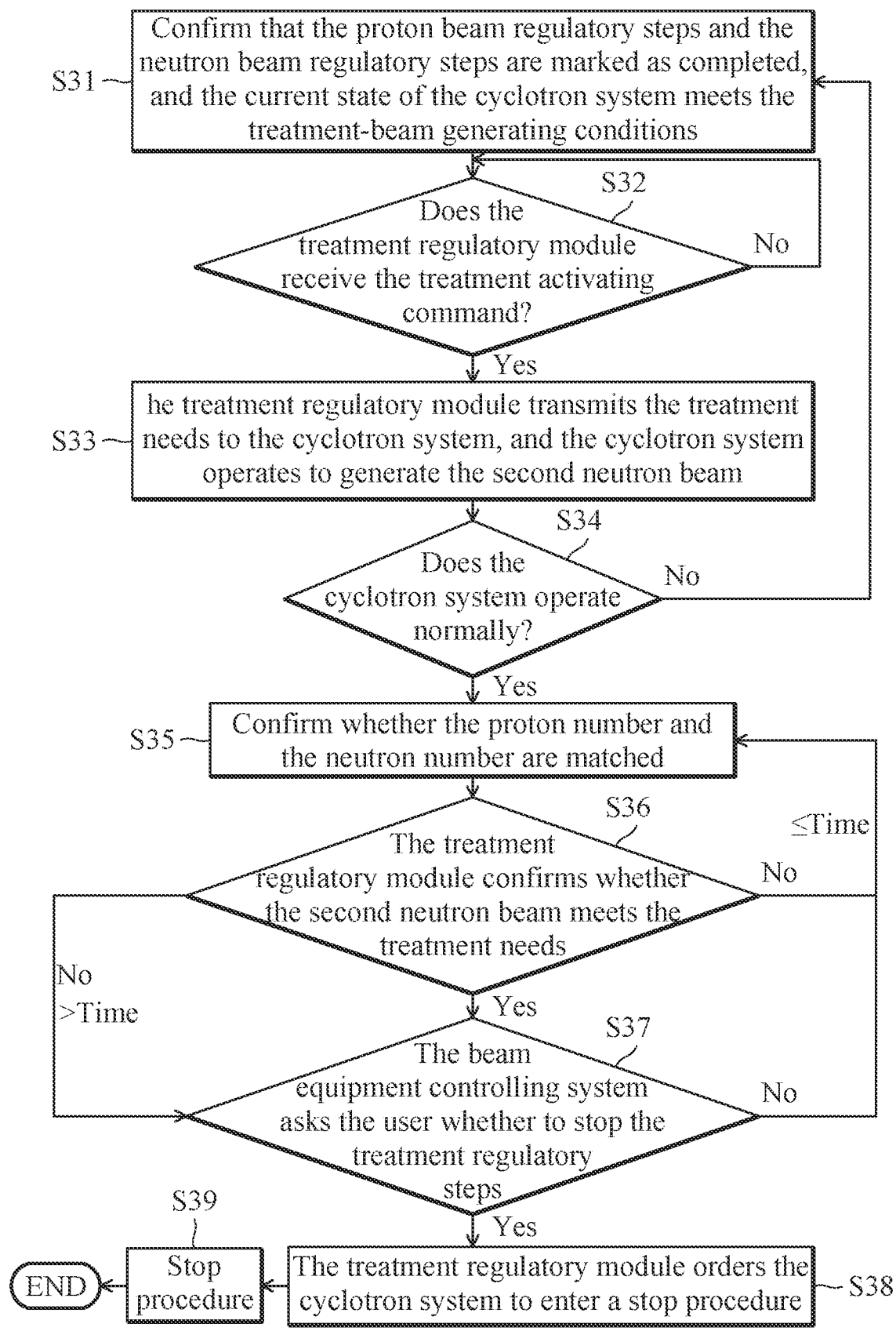
FIG. 5 illustrates a flow chart of treatment regulatory steps of the beam equipment controlling method of the embodiment 2 of the present invention.

Hereinafter, Embodiment 2 of the present invention will be described in detail with reference to FIG. 3 to FIG. 5.

Figure 3:
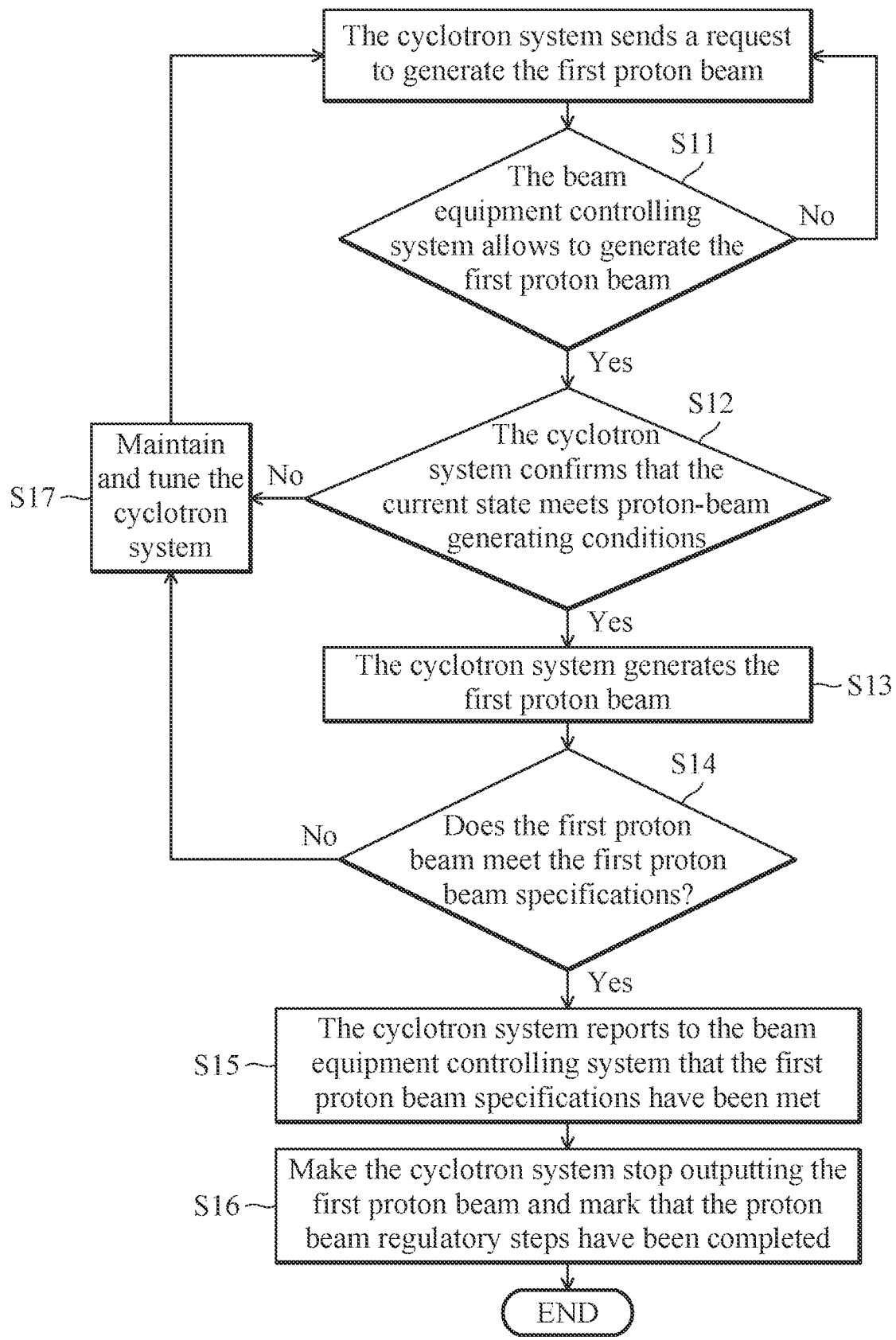
FIG. 3 illustrates a flow chart of proton beam regulatory steps of a beam equipment controlling method of an embodiment 2 of the present invention.

Referring to FIG. 3, the proton beam regulatory steps of Embodiment 2 of the present invention are described.

When the cyclotron system sends a request to the beam equipment controlling system to generate the first proton beam, the beam equipment controlling system allows the cyclotron system to generate the first proton beam (step S11). The beam equipment controlling system may first confirm whether safety conditions are met, and allow the cyclotron system to generate the first proton beam when the safety conditions are met. For example, the safety condition is that the user performs an input using an input device connected to the beam equipment controlling system after confirming that the environment is safe. Alternatively, the safety condition may be that the cyclotron system is not occupied by other courses of treatment or irradiation rooms.

After the beam equipment controlling system allows to generate the first proton beam, the cyclotron system confirms that the current state meets proton-beam generating conditions (step S12). That is, the cyclotron system confirms that it is a state where the proton beam can be generated at present. Taking the cyclotron system shown in FIG. 2 as an example, the proton-beam generating conditions include that the first Faraday cup FC1 is turned on and the second Faraday cup FC2 is turned off. In addition, when the cyclotron system cannot meet the proton-beam generating conditions within a period of time, it may notify the beam equipment controlling system to maintain and tune the cyclotron system (step S17).

After the cyclotron system confirms that the current state meets the proton-beam generating conditions, the cyclotron system generates the first proton beam (step S13). The cyclotron system controls an ion source to inject the current to generate a current proton beam as the first proton beam for testing.

Next, the cyclotron system confirms whether the first proton beam meets the first proton beam specifications (step S14). In the present embodiment, the first proton beam specifications include that a value of the continuous wave current transformer reaches the set value, and a value of the beam profile monitor meets the specifications. When the first proton beam does not meet the first proton beam specifications within a period of time, the beam equipment controlling system may be notified to maintain and tune the cyclotron system (step S17).

When the cyclotron system confirms that the first proton beam meets the first proton beam specifications, it reports to the beam equipment controlling system that the first proton beam specifications have been met (step S15). Next, the beam equipment controlling system makes the cyclotron system 13 stop outputting the first proton beam (cancels the allowance of the cyclotron to generate the first neutron beam, and turns off the cyclotron system), and then marks that the proton beam regulatory steps have been completed (step S16). The way for marking that the steps have been completed may include, for example, creating a memory space for marking that whether the proton beam regulatory steps, the neutron beam regulatory steps, and the treatment regulatory steps have been completed in a memory readable for the processing device, and marking with values 0 and 1. The steps that have been completed are marked as 1, the steps that not have been completed are marked as 0, and the default value is 0. Alternatively, the marking described above can also be stored in the storage device 12.

After the proton beam regulatory steps are marked as completed, enter the neutron beam regulatory steps. The beam equipment controlling system requests the cyclotron system to generate the first neutron beam (step S21). At this time, the cyclotron system confirms that the current state meets the neutron-beam generating conditions (step S22). That is, the cyclotron system confirms that it is a state where the neutron beam can be generated at present. Taking the cyclotron system shown in FIG. 2 as an example, the neutron-beam generating conditions include that the first Faraday cup FC1 is turned on and the second Faraday cup FC2 is turned on.

When the cyclotron system cannot meet the neutron-beam generating conditions within a period of time, it may notify the beam equipment controlling system to maintain and tune the cyclotron system (step S27). When the cyclotron system confirms that the neutron-beam generating conditions are met, the cyclotron system controls the ion source ISIS to inject the current to generate the first neutron beam as a neutron beam for testing (step S23).

Next, the beam equipment controlling system confirms whether the first neutron beam meets the first neutron beam specifications (step S24). In the present embodiment, the first neutron beam specifications include neutron intensity. Whether the first neutron beam meets the neutron intensity can be confirmed by using a neutron intensity detector connected with the beam equipment controlling system.

When the first neutron beam does not meet the first neutron beam specifications within a period of time, the beam equipment controlling system notifies the cyclotron system to maintain and tune the cyclotron system (step S27). When the first neutron beam meets the first neutron beam specifications, the beam equipment controlling system makes the cyclotron system stop outputting the first neutron beam (the beam equipment controlling system cancels the allowance to generate the first neutron beam, and notifies the cyclotron system to turn off)(step S25). After the ion source, the first Faraday cup, and the second Faraday cup are turned off, the cyclotron system notifies the beam equipment controlling system that the cyclotron system has been turned off. The beam equipment controlling system marks that the neutron beam regulatory steps have been completed (step S26).

After the proton beam regulatory steps and the neutron beam regulatory steps are marked as completed, enter the treatment regulatory steps. First, it is confirmed that the proton beam regulatory steps and the neutron beam regulatory steps are marked as completed, and the current state of the cyclotron system meets the treatment-beam generating conditions (step S31).

Next, the beam equipment controlling system waits for the treatment activating command from the user (step S32). For example, the beam equipment controlling system waits for the user to input a specific parameter or press a specific button to input the treatment activating command into the beam equipment controlling system. In addition, while waiting for the treatment activating command, the beam equipment controlling system may also require the user to input treatment needs. The treatment needs are specifications of the treatment neutron beam (the second neutron beam), and are determined according to the treatment plan instructed by the doctor. In the present embodiment, the treatment needs are the tumor prescription dose and the treatment plan instructed by the doctor. In addition, the beam equipment controlling system can calculate the required treatment time according to the treatment needs input by the user.

When the beam equipment controlling system receives the treatment activating command issued by the user, the beam equipment controlling system orders the cyclotron system to control the ion source ISIS to inject the current, and transmits the treatment needs to the cyclotron system to make the cyclotron system start to generate the second neutron beam (step S33). At this time, it is confirmed whether the cyclotron system operates normally (step S34). If the cyclotron system cannot operate normally within a period of time, the cyclotron system notifies the beam equipment controlling system. The user (e.g., medical personnel) decides whether to stop the treatment according to the received information.

If the cyclotron system operates normally, the cyclotron system confirms whether the proton number and the neutron number are matched (step S35). In some embodiments, it may measure the proton number through the continuous wave current transformers CWCT1 and CWCT2 respectively to obtain the first current value or the second current value. It may also measure the neutron number through the neutron intensity detector to obtain the neutron counting rate. In some embodiments, the neutron number can be derived from the pulsation number measured in the proportional counter. In addition, before the preset irradiation time ends, the beam equipment controlling system continuously confirms whether the generated second neutron beam meets the treatment needs through the neutron intensity detector (step S36).

When the irradiation time reaches the preset irradiation time, the beam equipment controlling system asks the user whether to stop the treatment regulatory steps (step S37). The user can extend the irradiation time according to the requirement, and return to the step S35.

If the user issues an order of stopping the treatment to the beam equipment controlling system, the beam equipment controlling system orders the cyclotron system to enter a stop procedure to stop outputting the second neutron beam (step S38). In the present embodiment, the stop procedure includes detecting whether the cyclotron system has stopped outputting the second neutron beam. In addition, after the cyclotron system stops outputting the second neutron beam, the beam equipment controlling system marks that the treatment regulatory steps have been completed.

There are many ways can be used to implement the stop procedure. For example, the beam equipment controlling system can continuously order the cyclotron system to stop and detect whether the cyclotron system has been turned off. If the cyclotron system is not turned off within a period of time (e.g., 2 minutes), an emergency stop procedure is initiated. The stop procedure is not limited thereto, it may design different stop procedure according to the requirement.

Although the plurality of embodiments have been described separately, the embodiments described above may also be implemented in combination. Alternatively, one of the plurality of embodiments may be partially implemented. Alternatively, the plurality of embodiments may be partially combined. In addition, the configurations and steps described in the plurality of embodiments described above can be partially modified according to the requirement.

The various aspects of the embodiments described above are written to make the present invention easy to understand, and the above descriptions are not intended to limit the present invention. Therefore, each element disclosed in each of the various aspects of the embodiments described above is intended to include all design variants or equivalents within the technical scope of the present invention.

What is claimed is:

1. A beam equipment controlling system for controlling a cyclotron system, the beam equipment controlling system comprises:
    a storage device, configured to store a treatment controlling application program;
    at least one processor, configured to execute the treatment controlling application program to implement following modules:
    a proton beam regulatory module, performing following steps when the proton beam regulatory module is implemented:
        determining whether to allow the cyclotron system to generate a first proton beam; and
        after confirming that the first proton beam meets first proton beam specifications, making the cyclotron system stop outputting the first proton beam and marking that a proton beam regulatory step has been completed;
    a neutron beam regulatory module, performing following steps when the neutron beam regulatory module is implemented:
        after confirming that the proton beam regulatory step is marked as completed and that a state of the cyclotron system meets neutron-beam generating conditions, allowing the cyclotron system to generate a first neutron beam;
        confirming that the first neutron beam meets first neutron beam specifications; and
        after making the cyclotron system stop outputting the first neutron beam, marking that a neutron beam regulatory step has been completed; and
    a treatment regulatory module, performing following steps when the treatment regulatory module is implemented:
        after confirming that the neutron beam regulatory step is marked as completed and that a state of the cyclotron system meets treatment-beam generating conditions, ordering the cyclotron system to generate a second neutron beam;
        confirming whether the second neutron beam meets treatment needs; and
        after making the cyclotron system stop outputting the second neutron beam, marking that a treatment regulatory step has been completed.

2. The beam equipment controlling system as claimed in claim 1, wherein:
    proton-beam generating conditions for the cyclotron system to generate the first proton beam comprise: a first Faraday cup is turned on, and a second Faraday cup is turned off;
    the neutron-beam generating conditions for the cyclotron system to generate the first neutron beam comprise: the first Faraday cup is turned on, and the second Faraday cup is turned on; and
    the treatment-beam generating conditions for the cyclotron system to generate the second neutron beam comprise: the first Faraday cup is turned on, and the second Faraday cup is turned on.

3. The beam equipment controlling system as claimed in claim 1, wherein the proton beam regulatory module confirming that the first proton beam meets the first proton beam specifications comprises confirming whether measurement results of a first beam profile monitor and a second beam profile monitor meet the first proton beam specifications.

4. The beam equipment controlling system as claimed in claim 1, wherein a the proton beam regulatory module confirming that the first proton beam meets the first proton beam specifications comprises confirming whether a current value of a first continuous wave current transformer and a current value of a second continuous wave current transformer meet the first proton beam specifications.

5. The beam equipment controlling system as claimed in claim 1, wherein the neutron beam regulatory module confirming that the first neutron beam meets the first neutron beam specifications comprises confirming whether a measurement result of a neutron intensity detector meets the first neutron beam specifications.

6. The beam equipment controlling system as claimed in claim 1, wherein the treatment regulatory module confirming whether the second neutron beam meets treatment needs comprises confirming whether a neutron counting rate of the cyclotron system meets a preset neutron number condition.

7. The beam equipment controlling system as claimed in claim 1, wherein the proton beam regulatory module confirms whether safety conditions are met before the beam equipment controlling system allows the proton beam to be generated.

8. A beam equipment controlling method for controlling a cyclotron system, the beam equipment controlling method comprises:
    proton beam regulatory steps, comprising:
        determining whether to allow the cyclotron system to generate a first proton beam; and
        after confirming that the first proton beam meets first proton beam specifications, making the cyclotron system stop outputting the first proton beam and marking that the proton beam regulatory steps have been completed;
neutron beam regulatory steps, comprising:
  after confirming that the proton beam regulatory steps are marked as completed and that a state of the cyclotron system meets neutron-beam generating conditions, allowing the cyclotron system to generate a first neutron beam;
  confirming that the first neutron beam meets first neutron beam specifications; and
  after making the cyclotron system stop outputting the first neutron beam, marking that the neutron beam regulatory steps have been completed; and
treatment regulatory steps, comprising:
  after confirming that the neutron beam regulatory steps are marked as completed and that a state of the cyclotron system meets treatment-beam generating conditions, ordering the cyclotron system to generate a second neutron beam;
  confirming whether the second neutron beam meets treatment needs; and
  after making the cyclotron system stop outputting the second neutron beam, marking that the treatment regulatory steps have been completed.

9. The beam equipment controlling method as claimed in claim 8, wherein:
  proton-beam generating conditions for the cyclotron system to generate the first proton beam comprise: a first Faraday cup is turned on, and a second Faraday cup is turned off;
  the neutron-beam generating conditions for the cyclotron system to generate the first neutron beam comprise: the first Faraday cup is turned on, and the second Faraday cup is turned on; and
  the treatment-beam generating conditions for the cyclotron system to generate the second neutron beam comprise: the first Faraday cup is turned on, and the second Faraday cup is turned on.

10. The beam equipment controlling method as claimed in claim 8, wherein the confirming that the first proton beam meets the first proton beam specifications comprises confirming whether measurement results of a first beam profile monitor and a second beam profile monitor meet the first proton beam specifications.

11. The beam equipment controlling method as claimed in claim 8, wherein the confirming that the first proton beam meets the first proton beam specifications comprises confirming whether a current value of a first continuous wave current transformer and a current value of a second continuous wave current transformer meet the first proton beam specifications.

12. The beam equipment controlling method as claimed in claim 8, wherein the confirming that the first neutron beam meets the first neutron beam specifications comprises confirming whether a measurement result of a neutron intensity detector meets the first neutron beam specifications.

13. The beam equipment controlling method as claimed in claim 8, wherein the confirming whether the second neutron beam meets treatment needs comprises confirming whether a neutron counting rate of the cyclotron system meets a preset neutron counting rate.

14. The beam equipment controlling method as claimed in claim 8, wherein during the proton beam regulatory steps, a confirmation is made as to whether safety conditions are met before allowing the cyclotron system to generate the first neutron beam.

* * * * *